United States Patent [19]

Caignard et al.

[11] Patent Number: 4,558,060
[45] Date of Patent: Dec. 10, 1985

[54] BENZOXAZOLINONES

[75] Inventors: Daniel H. Caignard, Chamalieres; Charles Lespagnol, Lambersart; Daniel Lesieur, Gondecourt; Norbert Busch, Manzat, all of France

[73] Assignee: Riom Laboratories - Cerm S.A., Riom, France

[21] Appl. No.: 554,194

[22] Filed: Nov. 22, 1983

[30] Foreign Application Priority Data

Nov. 25, 1982 [FR] France ................................. 82 19812

[51] Int. Cl.⁴ ..................... C07D 263/58; A61K 31/42
[52] U.S. Cl. ...................................... 514/375; 548/221
[58] Field of Search ........................ 548/221; 424/272; 514/375

[56] References Cited

FOREIGN PATENT DOCUMENTS

| 2491471 | 4/1982 | France ................................. 548/221 |
| 0123103 | 7/1982 | Japan ................................... 548/221 |
| 201186 | 4/1982 | European Pat. Off. ............. 548/221 |

Primary Examiner—George F. Lesmes
Assistant Examiner—S. A. Gibson

Attorney, Agent, or Firm—Abelman, Frayne, Rezac & Schwab

[57] ABSTRACT

The invention relates to compounds of the formula:

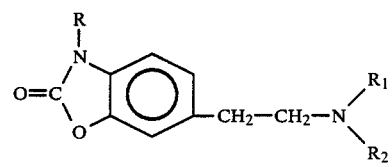

in which R represents hydrogen or a lower alkyl radical and $R_1$ and $R_2$ separately represent hydrogen, a lower alkyl, cycloalkyl or benzyl radical, or represent, together with the nitrogen atom to which they are bonded, a heterocyclic radical such as a morpholino, 4-(pyrimidin-2-yl)-piperazinyl or 4-phenylpiperazinyl the phenyl radical of which being optionally substituted by halogen, lower alkoxy or trifluoromethyl, having CNS activity and particularly hypnotic properties.

Moreover the compounds in which $R_1$ and $R_2$ are hydrogen can be used in the treatment of heart failure.

5 Claims, No Drawings

BENZOXAZOLINONES

The present invention relates to new benzoxazolinone derivatives substituted in the 6-position by a 2-aminoethyl chain and more particularly to compounds of general formula I:

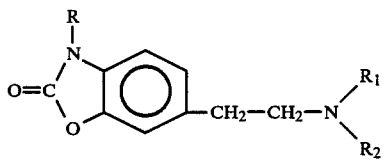

and pharmaceutically acceptable salts thereof, in which R represents hydrogen or a lower alkyl radical and $R_1$ and $R_2$ separately represent hydrogen, lower alkyl, cycloalkyl or benzyl, or represent, together with the nitrogen atom to which they are bonded, a heterocyclic radical, such as a morpholino, 4-(pyrimidin-2-yl)-piperazinyl or 4-phenylpiperazinyl the phenyl radical of which being optionally substituted by halogen, lower alkoxy or trifluoromethyl.

The compounds of formula I possess CNS-activity and more particularly hypnotic properties. In addition to that the compounds of formula I, in which $R_1$ and $R_2$ both are hydrogen, may be used in the treatment of heart failure.

The invention therefore also relates to the use of the compounds I as active principle in a pharmaceutical preparation.

The invention further relates to a process for the preparation of the said compounds, characterised by condensing an amine $HNR_1R_2$ with a 6-(2-halogenethyl)-benzoxazolinone, suitably substituted by R according to the following equation:

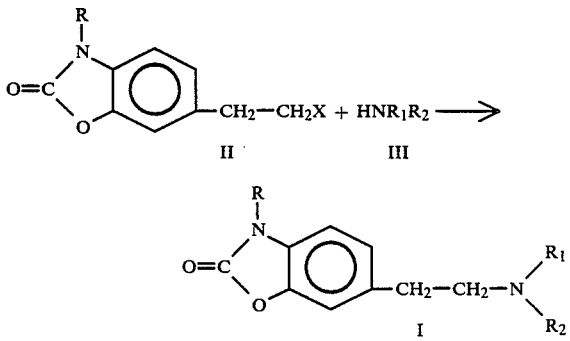

(X=halogen).

The reaction takes place in a suitable organic solvent; this solvent is preferably dioxane, but also other solvents may be used such as chloroform, acetonitrile, benzene or an alcohol.

The reaction is preferably carried out by using a slight excess of amine $NHR_1R_2$ and by heating the reaction mixture at the reflux temperature of the solvent. After cooling, the precipitate formed is stirred in a solution of sodium hydroxide. In the case where R represents hydrogen, the compound of the invention dissolves and it is precipitated again by changing back to an acid medium, for example by bubbling a stream of carbon dioxide.

In the particular case where $R_1$ and $R_2$ represent hydrogen, the corresponding compounds are advantageously obtained either by reacting hexamethylenetetramine with the 6-(2-halogenoethyl)-benzoxazolinone, followed by hydrolysis by heating in an acid medium, or by catalytic hydrogenation of the benzyl homologues of formula I ($R_1=R_2=$—$CH_2C_6H_5$) using for example Pd/charcoal as a catalyst. The latter method can also be used advantageously if $R_1=H$ and $R_2=$alkyl, starting from the monobenzyl homologue I ($R_1=$—$CH_2$—$C_6H_5$; $R_2=$alkyl).

The 6-(2-halogenoethyl)-benzoxazolinone derivative of formula II used as the starting material can, for example, be prepared from the corresponding 6-halogenoacetylbenzoxazolinone by reaction with triethylsilane in the presence of trifluoroacetic acid.

Pharmaceutically acceptable salts of the compounds I are derived from organic or inorganic acids, such as hydrochloric acid, hydrobromic acid, acetic acid, maleic acid, methanesulfonic acid, tartaric acid, fumaric acid, citric acid.

By "lower alkyl" in the definition of R, $R_1$ and $R_2$ is to be understood an alkyl group with 1 to 6 carbon atoms and preferably with 1–4 C-atoms, such as methyl, ethyl, isopropyl, propyl, butyl, isobutyl.

A cycloalkyl group has 3–7 carbon atoms, such as cyclopropyl, cyclopropylmethyl, cyclobutylmethyl, and cyclohexyl.

The heterocyclic radical in the definition of $R_1$ and $R_2$ is preferably a 5- or 6-membered heterocyclic ring which may contain a further hetero-atom such as nitrogen or oxygen. Where a second nitrogen is present in the heterocyclic ring this nitrogen atom may be substituted. Suitable heterocyclic radicals according to the invention are morpholino, piperazinyl, 4-(pyrimidin-2-yl)-piperazinyl and 4-phenylpiperazinyl, whereby the phenyl group may be substituted by halogen, alkoxy (1–4 C) or $CF_3$.

The acute toxicity and central nervous system activity of the compounds of the invention were investigated in mice using various test-models. These tests were carried out in accordance with the procedures summarised below.

ACUTE TOXICITY

Male mice of the $OF_1$, IFFA, CREDO strain and having an average weight of 22±1 g, receive, by oesophagial intubation, a solution of arabic gum and distilled water ($\frac{1}{2}$-$\frac{1}{2}$) containing the compound to be studied, at a rate of 0.25 ml per 20 g of body weight. The symptomatology of the intoxication was observed and the mortality was recorded after 24 hours.

SPONTANEOUS MOTILITY

Groups of 4 mice prepared as above are placed in circular corridors intersected by infrared beams, making it possible to count the number of movements made by the animals. The number of movements is summed up after 20 minutes and the results are expressed as the percentage variation relative to the group of control animals, which have only received the vehicle (gum arabic/water).

HYPNOTIC ACTIVITY

Mice receive, by intraperitoneal administration, 0.25 ml per 20 g of body weight of a solution consisting of arabic gum and of 0.154M NaCl solution ($\frac{1}{2}$-$\frac{1}{2}$) containing 12.5 mg.kg.$^{-1}$ of the compound to be studied, and the "sleep induction time"—the time taken for the loss of righting reflex to appear after the animal has been placed in the dorsal decubitus position—and the "sleep time"—the duration of the above loss of reflex—are then noted. For this test, pentobarbital is given as a reference, administered at a dose of 50 mg.kg.$^{-1}$.

The results recorded are reported in Table II below:

TABLE I

| Compound No.* | Estimated LD 50 mg.kg$^{-1}$ | SPONTANEOUS MOTILITY | | HYPNOTIC ACTIVITY | |
|---|---|---|---|---|---|
| | | Dose mg.kg$^{-1}$ | Variation % | Sleep induction time in minutes | Sleep time in minutes |
| 3 | 1000 | 50 | −97.5 | | |
| 4 | 1200 | 12.5 | −11.9 | | |
| 7 | 1200 | 50 | −69.9 | | |
| 8 | 1000 | 25 | −93.5 | | |
| 9 | 600 | 6.25 | −93.2 | 18 ± 7.5 | 46.2 ± 15 |
| 10 | 1000 | 6.25 | −99.3 | 18.2 ± 4.3 | 86 ± 15 |
| 12 | 1200 | 50 | −28 | | |
| 15 | 1200 | 50 | −23.2 | | |
| 16 | 600 | 50 | −34.4 | | |
| 17 | 480 | 25 | −62.8 | | |
| 18 | 1000 | 6.25 | −98.8 | 26.9 ± 6 | 132 ± 25 |
| 19 | 1000 | 6.25 | −97 | 15.1 ± 2 | 78 ± 16 |
| pentobarbital | | | | 9.5 ± 2.2 | 48 ± 7 |

*see table II

These results show the compounds of the invention to exhibit a psychotropic activity with a psycholeptic aspect, and particularly a strong hypnotic activity (see the activity of the compounds 10, 18 and 19). These properties of the compounds of the invention, and of their therapeutically acceptable salts, render them extremely suitable to be used in human therapy for the treatment of sleep disorders and character and behaviour disorders.

In addition to the activity pattern described above the compounds of formula I, in which $R_1$ and $R_2$ both represent hydrogen have a particularly beneficial effect in the treatment of heart failure. The latter activity has been tested using a technique derived from Deitchman and Snyder, Arch.Int. Pharmacodyn. 250, 65 (1981).

After having been anaesthesized dogs under articicial respiration are connected with pieces of apparatus for continuous monitoring the left intraventicular pressure, the dP/dt max, the amplitude of the left ventricular contraction, the aortic capacity, the heart frequency and the arteric pressure.

Heart failure is induced by intravenous administration of pentobarbital at a dose of 20 mg per kg body weight per minute until a decrease of 50% of dP/dt max is obtained after which this level is maintained by pentobarbital administration at a dose of 0.4 mg/kg/min. Ten minutes after the beginning of this heart failure effect the products to be tested are administered. The results are compared with those obtained using Dopamine and Dobutamine as reference compounds.

The compounds (to be tested) were firstly administered intravenously and it was found that the compounds according to the invention produced the same variations of the hemodynamic parameters at a dose 10 times lwer than that of the reference compounds. Then the test was repeated by administering the products intraduodenally (I.D.). Dopamine and Dobutamine were administered at a dose of 10 mg/kg I.D. and the compounds of the invention at a dose of 1 mg/kg.

After 20 minutes the reference compounds did not show any variation of the hemodynamic parameters. However, in contrast to these results the compounds of the invention in which $R_1$ and $R_2$ are both hydrogen (No. 2 and 15) do show a strong positive inotropic effect, an increase of the aortic capacity and a recovery of the bradycardia and the hypotension induced by pentobarbital. In this respect the compound no. 2 is particularly useful because the effects continue for at least 60 minutes.

The compounds of the invention can be administered enterally or parenterally.

In combination with the usual pharmaceutical excipients, the compounds I are preferably administered at daily doses of between 10 and 500 mg, depending on the methods of administration.

PREPARATION OF STARTING PRODUCT 3-methyl-6-(2-bromoethyl)-benzoxazolinone 10.8 g (0.04 mol) of 3-methyl-6-bromoacetylbenzoxazolinone and 45.6 g (0.4 mol) of trifluoroacetic acid were introduced into a 100 cm$^3$ flask with a ground glass neck, and 10.5 g (0.09 mol) of triethylsilane were then introduced dropwise by means of a dropping funnel, with cooling. The reaction was left to proceed for 15 hours, with stirring, at ambient temperature, the reaction mixture was then poured into 500 cm$^3$ of iced water, and the precipitate obtained was filtered off, washed, dried and recrystallised from cyclohexane.

This gave 9.22 g of the title compound having a melting point of 104.5°–105.5° C.

The compound 6-(2-bromoethyl)-benzoxazolinone was prepared in a corresponding manner.

EXAMPLE 1

3-Methyl-6-(-[4-(4-fluorophenyl)-piperazin-1-yl]-ethyl)-benzoxazolinone 0.025 mol (4.5 g) of 1-(4-fluorophenyl)-piperazine and 0.02 mol (5.12 g) of 3-methyl-6-(2-bromoethyl)-benzoxazolinone, dissolved beforehand in 50 cm$^3$ of dioxane, were introduced into a 100 cm$^3$ flask with a ground glass neck, fitted with a reflux condenser, and the mixture was then heated under reflux for 72 hours, with stirring. After cooling, filtration and drying, 100 cm$^3$ of a 3% strength aqueous solution of sodium hydroxide were added to the precipitate obtained, and the mixture was stirred for 30 minutes. Filtration, drying and recrystallisation from toluene gave 4.6 g of the title product having a melting point of 161°–164° C.

EXAMPLE 2

3-Methyl-6-(2-[4-(2-methoxyphenyl)-piperazin-1-yl]-ethyl)-benzoxazolinone

By following the procedure indicated in Example 1, but starting from 5.12 g of 3-methyl-6-(2-bromoethyl)-benzoxazolinone and 4.82 g of 1-(2-methoxyphenyl)-piperazine, 4.78 g of the title product having a melting point of 137°–137.5° C. were obtained after crystallisation from cyclohexane.

EXAMPLE 3

6-(2-[4-(2-methoxyphenyl)-piperazin-1-yl]-ethyl)-benzoxazolinone 0.025 mol (4.82 g) of 1-(2-methoxyphenyl)-piperazine and 0.02 mol (4.85 g) of 6-(2-bromoethyl)-benzoxazolinone, dissolved beforehand in 50 cm$^3$ of dioxane, were introduced into a 100 cm$^3$ flask with a ground glass neck, fitted with a reflux condenser, and the mixture was then heated under reflux for 72 hours, with stirring. After cooling, filtration and drying, the precipitate formed was dissolved in a sufficient amount of a 3% aqueous solution of sodium hydroxide. A stream of carbon dioxide was then bubbled and the precipitate was filtered off, washed and dried. Recrystallisation from toluene gave 4.7 g of the title product having a melting point of 182°–184° C.

EXAMPLE 4

6-(2-[4-(pyrimidin-2-yl)-piperazin-1-yl]-ethylbenzoxazolinone

By following the procedure indicated in Example 3, but starting from 4.10 g of 1-(pyrimidin-2-yl)-piperazine and 4.85 g of 6-(2-bromoethyl)-benzoxazolinone, 4.2 g of the title product were obtained having a melting point of 189°–189.5° C.

EXAMPLE 5

3-Methyl-6-(2-aminoethyl)-benzoxazolinone(hydrochloride)

0.04 mol (5.60 g) of hexamethylenetetramine, dissolved beforehand in 55 cm$^3$ of chloroform, and 0.03 mol (7.7 g) of 3-methyl-6-(2-bromoethyl)-benzoxazolinone, dissolved beforehand in 30 cm$^3$ of chloroform, were introduced into a 250 cm$^3$ flask with a ground glass neck, fitted with a reflux condenser, and the mixture was then heated under reflux for 150 hours, with stirring. After filtration and drying, the precipitate was introduced into a flask with a ground glass neck, fitted with a reflux condenser, and 150 cm$^3$ of absolute alcohol and 30 cm$^3$ of concentrated hydrochloric acid were added. After the mixture had been heated under reflux for two hours, the solvent was removed and the residue was washed with absolute alcohol, dried and recrystallised from methanol.

This gave 4.46 g of the title compound, in the form of the hydrochloride, having a melting point of 243° C. (decomposition).

EXAMPLE 6

3-Methyl-6-(2-isopropylaminoethyl)-benzoxazolinone(hydrobromide)

0.2 mol (11.82 g) of isopropylamine and 0.02 mol (5.12 g) of 3-methyl-6-(2-bromoethyl)-benzoxazolinone, dissolved beforehand in 60 cm$^3$ of acetonitrile, were introduced into a 100 cm$^3$ flask with a ground glass neck, fitted with a reflux condenser, and the mixture was then heated under reflux for 15 hours, with stirring. Cooling, filtration, drying and recrystallisation from 95° strength alcohol gave 5.36 g of the title compound, in the form of the hydrobromide, having a melting point of 265° C. (decomposition).

EXAMPLE 7

3-Methyl-6-[2-(N-benzyl-N-methylamino)-ethyl]-benzoxazolinone

By following the procedure indicated in Example 6, but starting from 0.04 mol (4.90 g) of N-benzyl-N-methylamine and 0.02 mol (5.10 g) of 3-methyl-6-(2-bromoethyl)-benzoxazolinone, 3.85 g of the title compound having a melting point of 72°–73° C. were obtained after recrystallisation from hexane.

EXAMPLE 8

3-Methyl-6-(2-methylaminoethyl)-benzoxazolinone(hydrochloride)

In a 1000 cm$^3$ flask with a ground glass neck, 0.025 mol (7.4 g) of the compound prepared in Example 7 was dissolved in 400 cm$^3$ of methanol, 0.35 g of palladium-on-charcoal was then introduced and the mixture was stirred under a hydrogen atmosphere at ordinary temperature and pressure. After the theoretical amount of hydrogen had been absorbed (560 cm$^3$ in ten hours), the reaction medium was filtered and the filtrate was concentrated and acidified with hydrogen chloride. Filtration of the precipitate and recrystallisation from methanol gave 4.55 g of the title compound, in the form of the hydrochloride, having a melting point above 265° C. (decomposition).

EXAMPLE 9

3-Methyl-6-(2-dipropylaminoethyl)-benzoxazolinone 2.02 g (0.02 mol) of N,N-dipropylamine and 2.56 g (0.01 mol) of 3-methyl-6-(2-bromoethyl)-benzoxazolinone, dissolved beforehand in 30 cm$^3$ of dioxane, were introduced into a 100 cm$^3$ flask with a ground glass neck, fitted with a reflux condenser, and the mixture was then heated under reflux for seventy-two hours, with stirring. After cooling, the reaction mixture was filtered and the filtrate was then evaporated in a water-bath, in vacuo. The residue was then taken up in 30 cm$^3$ of diethylether, the solution was filtered, the filtrate was washed with water and dried over calcium chloride, and a stream of hydrogen chloride was then bubbled. The precipitate formed was filtered off and then recrystallised from ethylacetate, and this gave 2.23 g of the title compound, in the form of the hydrochloride, having a melting point of 150°–152° C.

The compounds whose characteristics are indicated in Table II below were also prepared by the same processes.

TABLE II

| COMPOUND No. | R | $-N\begin{matrix}R_1\\R_2\end{matrix}$ | SALT | MELTING POINT, °C. |
|---|---|---|---|---|
| 1 (Example 6) | —CH$_3$ | —NH—CH$\begin{matrix}CH_3\\CH_3\end{matrix}$ | Hydrobromide | 265 (decomposition) |
| 2 (Example 5) | —CH$_3$ | —NH$_2$ | Hydrochloride | 243 (decomposition) |

TABLE II-continued $$-\text{N}\begin{array}{c}R_1\\R_2\end{array}$$

| COMPOUND No. | R | R₁/R₂ group | SALT | MELTING POINT, °C. |
|---|---|---|---|---|
| 3 | —CH₃ | piperazinyl-N-(3-CF₃-phenyl) | Base | 108.5–109.5 |
| 4 | —CH₃ | morpholino | Hydrochloride | 265 |
| 5 (Example 7) | —CH₃ | —N(CH₃)(CH₂-phenyl) | Base | 72–73 |
| 6 (Example 8) | —CH₃ | —NH—CH₃ | Hydrochloride | >265 (decomposition) |
| 7 | —CH₃ | piperazinyl-N-(pyrimidin-2-yl) | Base | 170.5–171.5 |
| 8 | —H | piperazinyl-N-(3-CF₃-phenyl) | Base | 146–148 |
| 9 (Example 2) | —CH₃ | piperazinyl-N-(2-OCH₃-phenyl) | Base | 137–137.5 |
| 10 (Example 3) | —H | piperazinyl-N-(2-OCH₃-phenyl) | Base | 182–184 |
| 11 | —H | —N(CH₃)(CH₂-phenyl) | Hemihydrate | 131–133 |
| 12 | —H | —NH—CH₃ | Hydrochloride | 265 (decomposition) |
| 13 | —H | —NH—CH(CH₃)₂ | Hydrobromide | 264 |

TABLE II-continued

| COMPOUND No. | R | -N(R1)(R2) | SALT | MELTING POINT, °C. |
|---|---|---|---|---|
| 14 | —H | —N(CH2-C6H5)2 | Base | 181–183 |
| 15 | —H | —NH2 | Hydrochloride | 265 (decomposition) |
| 16 | —CH3 | —NH—CH(CH2)(CH2) (cyclopropyl) | Hydrobromide | 250 (decomposition) |
| 17 (Example 4) | —H | —N(piperazinyl)-pyrimidinyl | Base | 189–189.5 |
| 18 (Example 1) | —CH3 | —N(piperazinyl)-C6H4-F | Base | 161–164 |
| 19 | —H | —N(piperazinyl)-C6H4-F | Base | 201–203 |
| 20 | —CH3 | —N(morpholinyl) | Base | 156–159 |
| 21 (Example 9) | —CH3 | —N(CH2—CH2—CH3)2 | Hydrochloride ⅔ H2O | 150–152 |

We claim:

1. A compound of the formula:

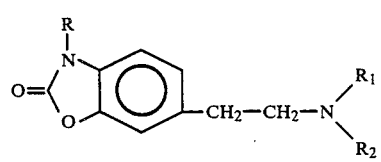

in which R represents hydrogen or a lower alkyl radical and $R_1$ and $R_2$ separately represent hydrogen, and pharmaceutically acceptable salts thereof.

2. A compound of the formula:

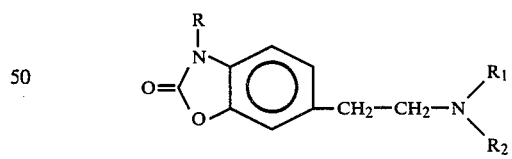

and pharmaceutically acceptable salts thereof, in which R represents hydrogen or a lower alkyl radical and $R_1$ and $R_2$ separately represent hydrogen, lower alkyl, cycloalkyl or benzyl and pharmaceutically acceptable salts thereof.

3. A compound according to claim 2, characterized in that $R_1$ represents hydrogen and $R_2$ represents a methyl, isopropyl or cyclopropyl radical, and the pharmaceutically acceptable salts thereof.

4. A compound according to claim 2 wherein $R_1$ and $R_2$ are both hydrogen, and the pharmaceutically acceptable salts thereof.

5. An anti-heart failure composition which comprises as the active principle, at least one compound as defined in claim 1 in combination with a pharmaceutically acceptable excipient.

* * * * *